United States Patent [19]
Sreenivasan et al.

[11] Patent Number: 6,129,907
[45] Date of Patent: Oct. 10, 2000

[54] STABLE HYDROGENATED LUPULONE ANTIBACTERIAL ORAL COMPOSITIONS

[75] Inventors: Prem K. Sreenivasan, Westfield; Nuran Nabi, Cranbury; Abdul Gaffar, Princeton, all of N.J.

[73] Assignee: Colgate Palmolive Company, New York, N.Y.

[21] Appl. No.: 09/366,892

[22] Filed: Aug. 4, 1999

[51] Int. Cl.[7] .................. A61K 7/16; A61K 7/18

[52] U.S. Cl. ................................. 424/49; 424/52

[58] Field of Search ........................... 424/49–58

[56] References Cited

U.S. PATENT DOCUMENTS

| | | | |
|---|---|---|---|
| 3,451,821 | 6/1969 | Todd et al. | 99/50.5 |
| 3,486,906 | 12/1969 | Todd | 99/50.5 |
| 3,615,660 | 10/1971 | Bavisotto et al. | 99/50.5 |
| 4,894,220 | 1/1990 | Nabi et al. | 424/52 |
| 5,334,375 | 8/1994 | Nabi et al. | 424/52 |
| 5,370,863 | 12/1994 | Barney et al. | 424/49 |
| 5,690,911 | 11/1997 | Mirajkar et al. | 424/49 |
| 5,800,803 | 9/1998 | Mirajkar et al. | 424/54 |

*Primary Examiner*—Shep K. Rose
*Attorney, Agent, or Firm*—Paul Shapiro

[57] ABSTRACT

A stable antibacterial oral composition containing a hydrogenated lupulone and an anionic surfactant.

11 Claims, No Drawings

STABLE HYDROGENATED LUPULONE ANTIBACTERIAL ORAL COMPOSITIONS

BACKGROUND OF THE INVENTION

1. Field of the Invention

This invention relates to a stable oral composition containing an effective antibacterial amount of a hydrogenated lupulone derived from beer hops.

2. The Prior Art

It is difficult to predict the efficacy of antibacterial agents when incorporated in any delivery vehicle and particularly in oral compositions. For example, dental plaque is a soft deposit which forms on teeth as opposed to calculus which is a hard calcified deposit on teeth. Unlike calculus, plaque may form on any part of the tooth surface, particularly at the gingival margin and is implicated in the occurrence of gingivitis. Cationic antibacterial compounds such as chlorhexidine, benzthonium chloride and cetyl pyridinium chloride have been used by the art as antibacterial antiplaque agents in oral compositions. However, such agents are generally not effective when there is also present in the oral composition an anionic surfactant required for the effective performance of oral compositions such as toothpaste and mouthrinses.

Beta-acids, also known as lupulones, derived from beer hops, are known to the art to exhibit antibacterial action in oral compositions. For example, U.S. Pat. No. 3,932,603 discloses that hop extract resins, such as lupulone and humulone, are effective as antimicrobials against cariogenic streptococci. U.S. Pat. No. 5,370,863 discloses oral compositions containing hop acids such as tetrahydroisohumulone which inhibit gram positive bacteria and plaque formation and periodontal disease.

Lupulones are also known to inhibit the growth of food pathogens, such as Listeria monocytogenes (U.S. Pat. Nos. 5,286,506; 5,455,038). In addition, the hydrogenated form, hexahydrolupulone, inhibits the growth of certain Lactobacilli (U.S. Pat. No. 5,082,975). Hydrogenated lupulones appear to be more active and stable than their non-hydrogenated parent compounds. For example, hexahydrocolupulone is believed to be more antibacterial active than colupulone while hexahydrolupulone has been found to be more stable than lupulone. Hexahydrocolupulone can be made by the chemical hydrogenation of colupulone using a number of methods known in the art. For example, hydrogenation can be achieved with platinum (IV) oxide as a catalyst as described by Riedl (Ber. 89:1863 (1956)) or by Carson (J. Am. Chem. Soc. 73:1850 (1951). A method for preparing hexahydrolupulone is described in U.S. Pat. No. 5,082,975.

As will hereinafter be demonstrated, a disadvantage to the use of hydrogenated lupulones in oral compositions such as dentifrices, is that the lupulone is not stable and separates into soluble and insoluble components on storage, this lack of stability discouraging commercial acceptance by consumers.

SUMMARY OF THE INVENTION

In accordance with the present invention there is provided a stable oral composition containing a hydrogenated lupulone which composition is prepared by admixing (1) a solution of the hydrogenated lupulone in a flavor oil and an aliphatic alcohol such as ethanol with (2) humectant solution containing an anionic surfactant and adjusting the pH to a range of about 8.0 to about 0.5 to prepare a premix and then adding the premix to the other ingredients of the oral composition.

The presence, in the hydrogenated lupulone containing oral composition, of an anionic polycarboxylate polymer such as a maleic anhydride/methyl vinyl ether copolymer, as will hereinafter be demonstrated, materially enhances the antibacterial properties of the oral composition.

DETAILED DESCRIPTION OF THE PREFERRED EMBODIMENTS

The term "hydrogenated lupulone" as used herein, includes within its meaning hydrogenated lupulones, derivatives and analogs thereof as well as pharmaceutically acceptable salts thereof. Hexahydrolupulone and hexahydrocolupulone and mixtures thereof are hydrogenated lupulones preferred in the practice of the present invention.

The hydrogenated lupulone used to prepare oral compositions of the present invention such as dentifrices, gels and mouthrinses is incorporated in the oral composition in an effective antiplaque amount, typically in a range of about 0.003 to about 2%, preferably about 0.02 to about 1% by weight. A mixture of hydrogenated lupulones namely hexahydrolupulone (35% by weight) and hexahydrocolupulone (65% by weight) is available commercially from Haas Hop Products, Washington, D.C.

When the oral composition is a gel or paste, such composition is prepared using an orally acceptable vehicle, including a water-phase with humectant which is preferably glycerine, sorbitol, an alkylene glycol or mixtures thereof wherein water is present typically in an amount of about 15 to about 40% by weight and glycerine, sorbitol and/or the alkylene glycol humectant typically total about 20 to about 75% by weight of the oral composition, more typically about 25 to about 60% by weight.

The vehicle of the oral paste or gel composition may also contain a dentally acceptable abrasive material such as sodium bicarbonate, sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof. The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose, sodium carboxymethyl cellulose and silica thickeners such as Sylodent 15.

In the embodiment of the present invention wherein the oral composition is substantially liquid in character such as a mouthwash or rinse, the vehicle is typically a water-alcohol mixture. Generally, the weight ratio of water to alcohol is in the range of from about 3:1 to 10:1 and preferably about 4:1 to about 6:1. The alcohol is a non-toxic alcohol such as ethanol or isopropanol. A humectant such as glycerin, sorbitol or an alkylene glycol or mixtures thereof, may be present in amount of about 10 to about 40% by weight. Mouthrinses typically contain about 50 to about 85% of water, about 0 to 20% by weight of a non-toxic alcohol and about 10 to about 40% by weight of the humectant.

Anionic surfactants are used in the oral compositions of the present invention to achieve increased prophylactic action and foaming. Unexpectedly, the presence of the anionic surfactant also plays a role in the stabilization of the hydrogenated lupulone. Suitable examples of anionic surfactants useful in the practice of the present invention include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

The anionic surfactant is present in the oral compositions of the present invention in an amount effective to stabilize the hydrogenated lupulone, which amount ranges from about 0.25 to about 3.0% by weight and preferably about 0.5 to about 2.0% by weight.

When surfactants other than anionic surfactants are used in hydrogenated lupulone containing oral compositions, the hydrogenated lupulone on storage is observed to be unstable.

Other agents which may be included in the oral composition of the present invention are fluoride salts to provide an anticaries effect, as for example, sodium fluoride, potassium fluoride, sodium monofluorophosphate and sodium hexafluorosilicate. The fluoride-ion providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

Antitartar agents such as sodium tripolyphosphate, tetrapotassium or tetrasodium pyrophosphate, or mixtures thereof, may be present in the oral compositions of the present invention at concentrations from about 0.5 to about 8% by weight.

Agents used to diminish teeth sensitivity such as potassium chloride, potassium nitrate and potassium citrate may also be included in oral compositions of the present invention at concentrations of about 0.1 to about 10% by weight.

Various other materials may be incorporated in oral compositions of this invention including preservatives, such as sodium benzoate, peroxide whitening compounds vitamins and chlorophyll compounds. These adjuvants, when present, are incorporated in the compositions in amounts which do not substantially adversely affect the properties and characteristics desired.

Flavoring oils useful in the practice of the present invention to dissolve the hydrogenated lupulone and to impart palatability to the oral composition include oil of spearmint, peppermint, wintergreen, sassafras, clove, sage, eucalyptus, cinnamon, lemon, and orange, and methyl salicylate.

Sweetening agents may also be present and include sucrose, lactose, maltose, xylitol, sodium cyclamate, perillartine, aspartyl phenyl alanine methyl ester and saccharine.

Suitably the flavor oil and sweetening agent each comprise from about 0.1% to 2% of the oral composition.

Antibacterial agents in addition to the hydrogenated lupulone may be included in the oral composition of the present invention and particularly noncationic halogenated diphenyl ethers agents which are desirable from considerations of effectiveness and safety such as 2',4,4' trichloro-2 hydroxydiphenyl ether (Triclosan) and 2,2'-dihydroxy-5,5' dibromophenyl ether. The antibacterial agent, when present in the oral composition is present in concentrations of about 0.05 to about 2% by weight and preferably 0.1 to about 1% by weight.

Anionic polycarboxylate polymers having a molecular weight of about 1,000 to about 5,000,000, preferably about 30,000 to about 500,000 in the form of their free acids or preferably partially or more preferably fully neutralized water soluble alkali metal (e.g. potassium and preferably sodium) or ammonium salts are included in the hydrogenated lupulone containing oral composition of the present invention to enhance the antibacterial efficacy of the hydrogenated lupulone. Preferred anionic polycarboxylate polymers are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other polycarboxylate polymers useful in the practice of the present invention are carboxyvinyl polymers commercially available, for example, under the trade designation Carbopol 934,940 and 941 from B.F. Goodrich, these polymers being comprised of a colloidally water-soluble polymer of polyacrylic acid crosslinked with from about 0.75% to about 2.0% of polyalkyl sucrose or polyalkyl pentaerythritol often with molecular weights of 4 to 5 million or more.

The anionic polycarboxylate polymer when employed in the oral composition of the present invention is incorporated in the composition in amounts of about 0.05 to about 5%, preferably about 0.1 to about 3% by weight.

To prepare the oral composition of the present invention a premix solution of the hydrogenated lupulone is prepared separately, wherein an aqueous solution containing about 2 to about 2.5% by weight of the anionic surfactant, preferably warmed to a temperature of 60 to 80° C., is admixed with an aqueous solution containing about 10 to about 15% by weight of one or more humectants such as glycerin, sorbitol or propylene glycol to provide a combined solution containing the hydrogenated lupulone in amounts of about 0.03 to about 0.3% by weight, the flavor oil in amounts of about 0.15 to about 1% by weight and an aliphatic alcohol such as ethanol or isopropanol in an amount of about 15 to about 25% by weight. Upon completion of admixing, the pH of the admixed solutions is adjusted to a pH of about 8 to about 10.5, preferably about 8.5 to about 9.5.

The oral compositions of the present invention may be prepared by suitably mixing the hydrogenated lupulone premix solution, prepared as previously described, with the other ingredients of the oral composition. For example, in the preparation of a mouthrinse, the premix of hydrogenated lupulone dispersed in the mixture of alcohol, humectant, surfactant, and flavor is added to an aqueous solution of any additional ingredients to be present in the mouthrisne and mixed under vacuum for about 15–30 minutes. The resulting rinse product is then packaged. Dentifrices are prepared similarly, additional thickener and polishing agents being included in the last or penultimate step.

The following Examples further illustrate the present invention, but it is understood that the invention is not limited thereto. All amounts and proportions referred to herein and in the appended claims are by weight unless otherwise indicated.

EXAMPLE I

A mouthrinse containing a mixture of hydrogenated lupulones, namely, hexahydrolupulone (35% by weight) and hexahydrocolupulone (65% by weight), the mixture hereinafter being referred to as "HHBA" was prepared. The ingredients of the mouthrinse are listed in Table I below. For the purpose of comparison, a hydrogenated lupulone containing a mouthrinse was prepared having the composition disclosed in U.S. Pat. No. 5,370,863, the ingredients of which are listed in Table II below.

TABLE I

| Ingredient | % by Weight |
| --- | --- |
| HHBA | 0.03 |
| Ethanol | 15.0 |
| Glycerin | 10.0 |
| Sodium lauryl sulfate | 0.75 |
| Sorbitol | 10.0 |
| Propylene glycol | 15.0 |
| Flavor oil | 0.1 |
| KOH (10%) | 0.2 |
| $KH_2PO_4$ (25%) | 0.1 |
| Distilled water q.s. ad. | 100.00 |

The HHBA premix used to prepare the mouthrinse was prepared as follows:

Stage I: The anionic surfactant sodium lauryl sulfate, was dissolved in warm (60–70° C.) water.

Stage II: A separate solution of HHBA dissolved in flavor oil, followed by the addition of ethanol, was prepared.

Stage III: A separate solution of sorbitol, propylene glycol and glycerin was prepared.

The solutions prepared in Stages I and III were admixed followed by admixing with the solution of Stage II. The pH of the combined solutions were adjusted to 7.0 with 10% KOH followed by further adjustment of the pH to 9.0 with 25% $K_2HPO_4$ to prepare the HHBA premix. The premix was then added to the remainder of the mouthrinse ingredients to prepare the mouthrinse of Table I.

The comparative mouthrinse of Table II was prepared as follows:

Stage I: Sodium saccharin and Pluronic F127 surfactant were dissolved in warm (60–70° C.) water. Next glycerol was added and mixed. Pluronic F127 surfactant is a polyoxyethylene/polyoxypropylene block copolymer nonionic surfactant available from BASF Corporation, Parsippany, N.J. 07064.

Stage II: HHBA was dissolved in flavor oil.

Stage III: A separate solution of ethanol and benzoic acid was prepared.

The solutions prepared in Stages I and III were admixed with the solution in Stage II. Thereafter the color and sodium hydroxide were added.

TABLE II

| Ingredient | % by Weight |
| --- | --- |
| Tetrahydroisohumulone | 0.0025 |
| Ethanol | 16.25 |
| Glycerin | 10.0 |
| Pluronic F127 | 0.12 |
| Benzoic acid | 0.05 |
| Sodium saccharin | 0.05 |
| Flavor oil | 0.15 |
| Color | 0.04 |
| Sodium hydroxide (10% sol.) | 0.15 |
| Distilled water q.s. ad. | 100.00 |

Stability Test

After being stored in sealed glass jars for 3 days at 22° C., the mouthrinse of Table I remained a clear, homogeneous solution, whereas the comparative mouthrinse of Table II when subjected to the same aging conditions, separation of the HHBA into soluble and insoluble components was observed.

EXAMPLE II

There is provided in Table III below the ingredients of a stable HHBA dentifrice containing a dicalcium phosphate abrasive prepared in the manner previously described.

TABLE III

| Ingredient | % by Weight |
| --- | --- |
| Glycerin | 10.0 |
| Carageenan gum | 0.8 |
| Sorbitol (70%) | 16.0 |
| HHBA | 0.2 |
| Sodium saccharin | 0.2 |
| Sodium fluoride | 0.25 |
| Dicalcium phosphate dihydrate | 48.0 |
| Sodium lauryl sulfate | 2.0 |
| Flavor oil | 1.0 |
| Polyethylene glycol 600 | 1.0 |
| Sodium monofluorophosphate | 0.76 |
| Tetrasodium pyrophosphate | 0.25 |

EXAMPLE III

There is provided in Table IV below, the ingredients of a stable HHBA dentifrice containing dicalcium phosphate and precipitated calcium carbonate abrasives prepared in the manner previously described.

TABLE IV

| Ingredient | % by Weight |
| --- | --- |
| Glycerin | 15.0 |
| Carageenan gum | 0.65 |
| Sorbitol (70%) | 10.0 |
| HHBA | 0.3 |
| Sodium Saccharin | 0.15 |
| Sodium Fluoride | 0.25 |
| Precipitated calcium carbonate | 36.0 |
| Dicalcium phosphate | 13.0 |
| Sodium lauryl sulfate | 2.3 |
| Flavor oil | 0.95 |
| Water q.s. | 100.00 |

EXAMPLE IV

The mouthrinse of Table I was tested using a microbiological assay, namely, Minimum Inhibitory Concentration (MIC) and bacterial growth inhibition on hydroxyapatite discs. The gram-positive oral bacterium *Actinomyces viscosus* was routinely grown overnight in trypticase soy broth (Difco Labs, Detroit, Mich.) at 37° C. A gram strain of the cultures was prepared to determine the purity of the cultures prior to in vitro testing of the mouthrinse.

MIC Assay

The bacterial strain grown for 18 hours at 37° C. in trypticase soy broth (TSB) was diluted in fresh broth to adjust its optical density between 0.1 and 0.2 absorption units at 610 nm prior to MIC determinations.

The mouthrinse of Table I and a placebo mouthrinse were diluted in TSB and the MIC was determined using the microtiter format according to standard procedures (Manual of Clinical Microbiology, 1995). The placebo mouthrinse was prepared in the same manner as the mouthrinse of Table I except HHBA was not included in the mouthrinse. The MIC results are recorded in Table V below.

Bacterial Growth Inhibition Assay on Hydroxyapatite Disks

The antiplaque effect of the mouth rinse of Table I and the placebo rinse described above were assessed by a growth inhibition test with A. viscosus using hydroxyapatite disks treated with the rinse and bacterial growth was monitored by measuring optical density (OD) at 610 nm after 2 hours and 24 hours after treatment of the disks. In this test, the hydroxyapatite disk was placed in a test tube containing clarified human saliva and incubated overnight at 37° C. Thereafter, the saliva was removed from the tube and replaced with mouthrinse solution and incubated for 30 minutes at 37° C. whereupon the disk was placed in a transparent plastic tube containing bacterial strains diluted in TSB to an OD of 0.25 at 610 nm. The results of the microbiological assays are recorded in Table VI below.

TABLE V

| Composition | MIC as a function of % rinse concentration for bacterial inhibition | MIC as a function of active concentration (in ppm) |
| --- | --- | --- |
| Table I Rinse | 0.39 | 2.3 |
| Placebo Rinse | 1.56 | — |

The results in Table V indicate that the HHBA mouthrinse of Table I was active against A. viscosus and provided better antibacterial efficacy than the placebo rinse.

TABLE VI

| Composition | Bacterial OD at 2 hrs. | Bacterial OD at 24 hrs. |
| --- | --- | --- |
| Table I Rinse | 0.3 | 0.5 |
| Placebo Rinse | 0.52 | 1.35 |

The results recorded in Table VI indicate that treatment with the mouthrinse of Table I resulted in fewer bacteria as determined by lower bacterial OD as compared to the placebo rinse.

Antibacterial Efficacy of Dentifrices

Zone of Bacterial Inhibition With Dentifrices

The antibacterial efficacy of the dentifrice of Table IV and a placebo dentifrice were assessed by a zone of bacterial inhibition test with A. viscosus. The placebo dentifrice was prepared in the same manner as the dentifrice of Table IV except HHBA was not included in the dentifrice. In this test, hydroxyapatite disks were treated with a HHBA containing dentifrice or the placebo and placed on an agar plate containing A. viscosus. The inhibition of bacterial growth around each disk zone was measured after 48 hours of incubation and the results are shown in Table VII below.

TABLE VII

| Composition | Zone of inhibition in centimeters |
| --- | --- |
| Table IV dentifrice | 2.17 |
| Placebo dentifrice | 1.77 |

The results recorded in Table VII indicate that the Table IV dentifrice had a higher zone of inhibition than the placebo dentifrice indicating antibacterial efficacy.

Bacterial Growth Inhibition on Hydroxyapatite

The antibacterial effects of the Table IV dentifrice was assessed by a growth inhibition test with A. viscosus. The placebo dentifrice was prepared in the same manner as the dentifrice of Table IV except HHBA was not included in the dentifrice. In this test, hydroxyapatite disks were treated with the dentifrice and bacterial growth monitored by measuring optical density at 610 nm after 24 post-treatment. The results are shown in Table VII below.

TABLE VIII

| Composition | Bacterial Optical Density at 610 nm 24 hours post-treatment |
| --- | --- |
| Table IV dentifrice | 0.43 |
| Placebo dentifrice | 0.91 |

The results recorded in Table VIII indicate the highest optical density (a measure of bacterial growth) was observed with the placebo dentifrice, and a lower optical density from disks treated with the Table IV dentifrice indicating that the HHBA containing dentifrice provided antibacterial efficacy.

EXAMPLE IV

There is provided in Table IX below, the ingredients of a stable HHBA dentifrice containing an anionic polycarboxylate polymer, Gantrez S-97.

TABLE IX

| Ingredient | % by Weight |
| --- | --- |
| Silica abrasive | 20.0 |
| Sylodent 15 | 1.5 |
| Glycerin | 20.0 |
| Iota carageenan | 0.4 |
| Sorbitol (70%) | 20.85 |
| HHBA | 0.3 |
| Sodium saccharin | 0.3 |
| Sodium fluoride | 0.243 |
| Sodium lauryl sulfate | 1.5 |
| Flavor | 1.0 |
| Propylene glycol | 0.5 |
| Titanium dioxide | 0.5 |
| Gantrez S-97 | 2.0 |
| Sodium carboxymethyl cellulose | 1.1 |
| Water | q.s. |

The antibacterial efficacies of the dentifrice of Table IX (Dentifrice Table IX) and a dentifrice identical to the dentifrice of Table IX except that Gantrez S-97 was absent from the dentifrice (Dentifrice C) were determined by examining the ability of each dentifrice to inhibit the growth of bacteria. For this test, a slurry of each dentifrice was prepared in water. The slurries were centrifuged and the resulting supernatant used to treat saliva coated hydroxyapatite disks for 30 minutes. The dentifrice treated hydroxyapatite disks were washed with water and incubated with a culture of *Actinomyces viscosus*. The growth of the culture was determined 24 hours after incubation with the dentifrice treated disks. The results from triplicate samples are shown in Table X below and indicate bacterial growth as determined by measuring the optical density of each culture at 610 nm. Water treated disks were used as a control.

TABLE X

| Treatment | Bacterial Optical Density at 610 nm |
|---|---|
| Dentifrice Table IX | 0.50 |
| Dentifrice C | 0.61 |
| Control | 1.49 |

The results recorded in Table X indicate that although the dentifrice containing 0.3% by weight HHBA (Dentifrice C) inhibits the growth of bacteria as evidenced by the lower bacterial optical density, the dentifrice containing HHBA and Gantrez (Dentifrice Table IX) is more effective in inhibiting bacterial growth.

What is claimed is:

1. A method for preparing a stable antibacterial oral composition containing a hydrogenated lupulone, the method comprising preparing a premix of (1) a solution of the hydrogenated lupulone in a mixture of flavor oil and an aliphatic alcohol with (2) a humectant solution containing an anionic surfactant adjusting the pH of the combined solutions to a range of 8.0 to 10.5 and then adding the premix to the other ingredients of the oral composition.

2. The method of claim 1 wherein the hydrogenated lupulone is present in the composition in an amount in the range of about 0.003 to about 2.0% by weight.

3. The method of claim 1 wherein the hydrogenated lupulone is hexahydrolupulone.

4. The method of claim 1 wherein the hydrogenated lupulone is hexahydrocolupulone.

5. The method of claim 1 wherein the hydrogenated lupulone is a mixture of hexahydrocolupulone and hexahydrolupulone.

6. The method of claim 1 wherein the anionic surfactant is sodium lauryl sulfate.

7. The method of claim 1 wherein the anionic surfactant is present in the composition in an amount effective to stabilize the hydrogenated lupulone.

8. The method of claim 1 wherein the anionic surfactant is present in the oral composition in an amount ranging from about 0.25 to about 3.0% by weight.

9. The method of claim 1 wherein an anionic polycarboxylate polymer is present in the oral composition in an amount of about 0.05 to about 5.0% by weight.

10. A stable oral composition prepared by the method of claim 1.

11. A method for preparing a stable antibacterial oral composition containing a hexahydrocolupulone, the method comprising preparing a premix of (1) a solution of the hexahydrocolupulone in a mixture of flavor oil and an aliphatic alcohol with (2) a humectant solution containing sodium lauryl sulfate adjusting the pH of the combined solutions to a range of 8.0 to 10.5 and then adding the premix to the other ingredients of the oral composition.

* * * * *